United States Patent [19]

Imran

[11] Patent Number: 5,211,174
[45] Date of Patent: May 18, 1993

[54] LOW IMPEDANCE, LOW DUROMETER, DRY CONFORMING CONTACT ELEMENT

[75] Inventor: Mir A. Imran, Palo Alto, Calif.

[73] Assignee: Physiometrix, Inc., Sunnyvale, Calif.

[21] Appl. No.: 582,749

[22] Filed: Sep. 14, 1990

[51] Int. Cl.$^5$ .................... A61B 5/04; A61N 1/05
[52] U.S. Cl. ..................... 128/639; 128/641; 128/786; 252/500
[58] Field of Search .................... 128/639–641, 128/643, 644, 784, 786, 798, 802, 803; 252/500, 514

[56] References Cited

U.S. PATENT DOCUMENTS

| | | | |
|---|---|---|---|
| 3,426,746 | 2/1969 | Seamens, Jr. | 128/640 |
| 3,606,881 | 9/1971 | Woodson | 128/641 |
| 4,008,721 | 2/1977 | Burton | 128/802 |
| 4,088,133 | 5/1978 | Twentier | 128/644 |
| 4,226,247 | 10/1980 | Hauser et al. | 128/641 |
| 4,237,886 | 12/1980 | Sakurada et al. | 128/798 X |
| 4,418,697 | 12/1983 | Toma | 128/640 |
| 4,848,348 | 7/1989 | Craighead | 128/798 X |
| 4,852,574 | 8/1989 | Inoue et al. | 128/643 |
| 4,865,039 | 9/1989 | Dunseath, Jr. | 128/640 |

FOREIGN PATENT DOCUMENTS

| | | | |
|---|---|---|---|
| 0000759 | 2/1976 | European Pat. Off. | 128/640 |
| 2521697 | 12/1975 | Fed. Rep. of Germany | 128/639 |
| 840242 | 6/1984 | World Int. Prop. O. | |

Primary Examiner—Lee S. Cohen
Attorney, Agent, or Firm—Flehr, Hohbach, Test, Albritton & Herbert

[57] ABSTRACT

Contact comprised of a mass of nonconductive material having a low durometer and conductive elements dispersed in the mass of material in sufficient quantity to establish contact between the elements to provide a resistivity in the range of 10 to 100 ohm-cm.

20 Claims, 1 Drawing Sheet

LOW IMPEDANCE, LOW DUROMETER, DRY CONFORMING CONTACT ELEMENT

This invention relates to a low impedance, low durometer, dry conforming contact element and method and device using the same.

Electrodes of various types have heretofore been provided. For example, there are a number of electrodes which have been making ECG measurements. Typically, such electrodes have been of the disposable type and have been provided with a small foam pad which has been impregnated with a potassium chloride solution. This potassium chloride pad makes contact with the skin when it is in use. Before use, typically the device is covered with a plastic sheet to, in effect, enclose the same in an airtight vacuum to prevent it from drying out before use. To use the same, the plastic sheet is removed and the potassium chloride impregnated pad is brought into contact with the skin and held in contact therewith by a surrounding pad which is covered with an adhesive. Such electrodes have been found to have a number of disadvantages. They tend to dry out rather rapidly when placed into use. The impedance of the electrodes is fairly high in the range of 100-500,000 ohms, which increases as the pads dry out. In addition, it has been found that the potassium chloride solution has a tendency to irritate the skin and often gives patients a rash when worn more than several hours. This last undesirable characteristic is particularly noteworthy in the case of premature infants who have very sensitive skin. There is therefore a need for a new and improved contact element which overcomes the above disadvantages.

In general, it is an object of the present invention to provide a contact element which has low impedance, has a low durometer and is dry, and a device and method for making the same.

Another object of the invention is to provide a contact element of the above character which can be utilized in various devices, as for example ECG electrodes and pacemaker leads.

Another object of the invention is to provide a contact element of the above character which can be preformed into a desired shape.

Another object of the invention is to provide a contact element which can be formed from a putty-like material.

Another object of the invention is to provide a contact element of the above character which is very passive chemically and will not react with the skin.

Another object of the invention is to provide a contact element of the above character which can be worn for long periods of time by the patient without causing irritation or skin rashes.

Another object of the invention is to provide a contact element of the above character which is relatively inexpensive and which can be manufactured economically.

Additional objects and features of the invention will appear from the following description in which the preferred embodiments are set forth in detail in conjunction with the accompanying drawings.

In general, it is an object of the present invention to provide a contact element comprising a mass of nonconductive material having a low durometer and conductive elements disposed in the mass of material in sufficient quantity to establish contact between the elements so that the resistivity of the contact element ranges between 10-100 ohms-cm. The nonconductive material is in the form of a silicone gel which retains its stickiness after it has cured.

Figure 1:
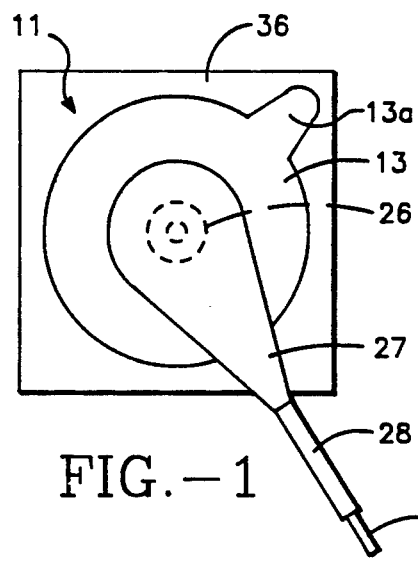
FIG. 1 is a top plan view of an electrode incorporating a contact element of the present invention.
Figure 2:
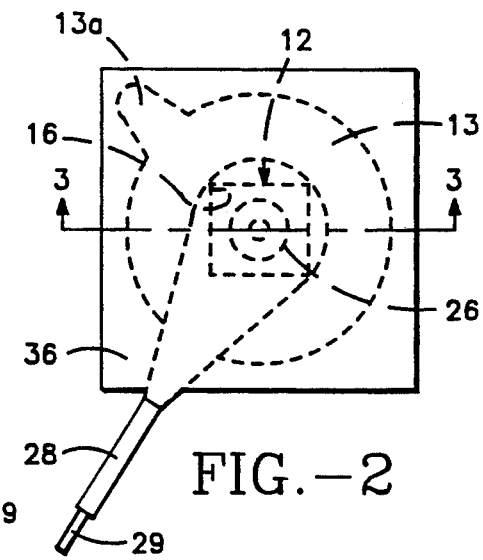
FIG. 2 is a bottom plan view of the contact element shown in FIG. 1.
Figure 3:
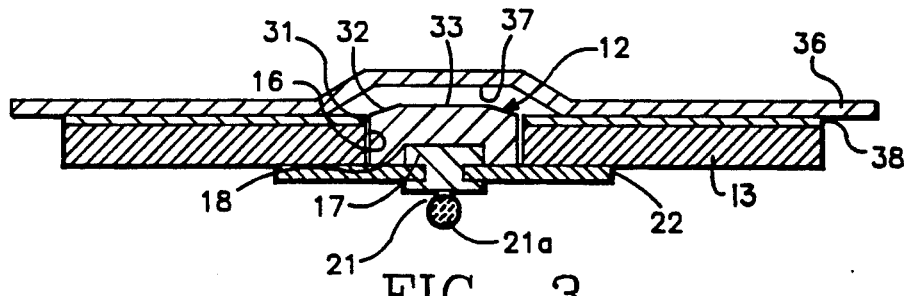
FIG. 3 is a cross-sectional view taken along the line 3—3 of FIG. 2.

More specifically, in FIGS. 1, 2 and 3, an ECG electrode 11 is shown which incorporates therein a conductive silicone contact or element 12 incorporating the present invention. The electrode 11 is comprised of a flexible pad 13 formed of a suitable material such as a foam plastic. The pad 13 has a suitable configuration as for example circular with a dimension of approximately 1½ inches and a thickness of approximately 1/16th to ⅛th inch. The pad is provided with a tab portion 13a. The pad 13 is provided with a centrally disposed rectangular recess or opening 16. If desired, other geometries such as circular can be used.

A conventional conductive circular button 17 is disposed within the recess 16 and is formed of a suitable conducting material such as stainless steel which is covered by a conductive coating 18 of a suitable type such as silver chloride coating. The button 17 is retained in the recess 16 in a suitable manner such as by securing the same to a conventional metal snap 21 which is secured to a flexible sheet 22 of relatively strong material such as a conventional plastic such as polyethylene or polysulfone by clamping the two parts comprised of the button 17 and the snap 21 onto the sheet 22. The outer margin of the sheet 22 extends over the recess 16 and over the inner margin of the pad 13 and is bonded to the pad 13 so as to support the button 17 within the recess 16. As shown in FIG. 3, the snap 21 is in the form of a male snap having a spherical protrusion 21a which is adapted to receive and engage a cooperating metal female snap 26 and frictionally engage the same and to make electrical contact therewith. The female snap 26 is carried by a termination 27 formed of a suitable material such as plastic which has a lead 28 bonded therein which carries a conductor 29 that is connected to the female snap 26.

The conductive silicone contact or element 12 is also disposed within the recess 16 and is in intimate contact with the button 17. The contact 12 can have any desired conformation. It is, as shown in FIGS. 2 and 3, is substantially rectangular in configuration of a size which is slightly less than the size of the recess 16. It is formed with a side wall 31 which fits within the recess 16. It is also provided with a tapered surface 32 which adjoins the sidewall 31 and also adjoins a generally planar contact surface 33.

Protective means is provided for protecting the conductive contact 12 from contamination prior to use and consists of a sheet 36 of a relatively flexible material such as plastic which is impervious to air. As shown, the sheet 36 can have any desired configuration as for example rectangular as shown in the drawings. This sheet is provided with a centrally disposed cup 37 which is adapted to receive the protruding surface 33 of the contact 12 when the sheet 36 is mounted on the pad 13. The pad 13 is provided with an adhesive 38 which is utilized for removably retaining the sheet 36 in engagement with the pad 13. The adhesive is also of a type which facilitates adhering the pad to the skin of a patient when the contact is in use. Adhesives of this type are well known to those skilled in the art and will not be described in detail.

The conductive silicone contact 12 is formed of a conductive silicone. The silicone when cured is characterized in that it is dry and is very soft. It is nonconducting and has a tacky surface to the feel.

Figure 7:
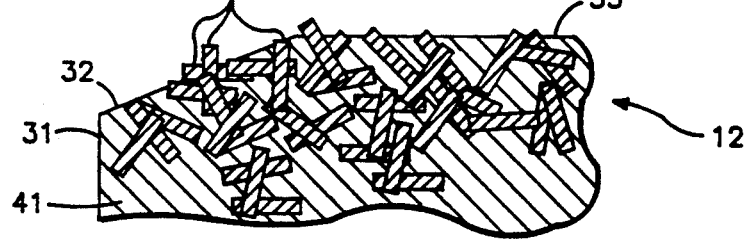
FIG. 7 is a greatly enlarged microscopic view of a portion of the contact element incorporating the present invention.

A silicone found to be particularly suitable for use in the present application is a two-component or two part system low viscosity liquid silicone gel manufactured by General Electric Company Silicone Products, Waterford, New York 12188, identified as an RTV 6157 silicone gel. It cures at room temperature by use of a curing agent in a ratio of approximately 15 to 6:1. A softer gel is obtained by using less curing agent. It is free of solvents. It is transparent with a refractive index of 1.4. The cured gel permits a mechanical penetration of 8 mm with a Universal Penetrometer having a 69.5 gram aluminum shaft. As hereinafter described, when the gel and the catalyst are mixed together a silicone mass 41 is provided as shown in FIG. 7 in which conductive elements 42 are disposed. The conductive elements are formed of a material which is nonreactive to body fluids.

One type of conductive element found to be particularly suitable for use in the present invention is a silver-coated particle manufactured by Potters Industries Inc., Waterview Corporate Center, 20 Waterview Boulevard, Parsippany, New Jersey 07054, which can take the form of silver-coated fibers, silver-coated inorganic flakes, or silver-coated glass spheres. It has been found that the silver-coated cylindrical glass fibers provide the most desirable characteristics, followed by silver-coated inorganic flakes. The conductive elements 42 are in the form of silver-coated glass rods or cylinders 42. These silver-coated fibers combine the high conductivity of silver with the lightweight reinforcing properties of the fibers. Particle size can range from 15 to 100 microns in any dimensions. The particles have a silver coating which ranges from 2 to 6 percent silver by weight. Silver-coated glass fibers are utilized because they permit better conductivity because the fibers tend to contact each other more readily than would silver-coated glass spheres. For example, these can have a diameter of 5 to 20 microns and a length of 20 to 100 microns to any length (L) over diameter (D) ratio of 20 or less. The silver-coated glass flakes also provide a good conductivity, but not as good a conductivity as the silver-coated fibers. By way of example, a silver-coated boro-silicate glass high-temperature ceramic can have a silver thickness ranging from 100 to 250 Å to provide a powder resistivity of 0.070 ohm-cm. Thicker coatings, as for example silver-coating constituting 6 percent by weight, provide a 520 Å silver thickness with a conductivity of 0.006 ohm-cm. The silver-coated glass fibers can constitute a suitable percentage by weight of the composition which forms the pad 12, as for example 60 to 85 percent by weight of the total composition or mass with the silicone comprising the balance.

The silicone gel and the catalyst are in liquid form. They are poured into a suitable container and are stirred while the silver-coated glass fibers are mixed into the silicone to provide a thick paste-like consistency. The mixture is then dispensed through a syringe-like device into a suitable mold (not shown) having the conformation that is desired for the silicone contact 12. It is cured at a suitable temperature, as for example room temperature or at a suitable elevated temperature of 60° to 75° C. for a period of time ranging from 45 minutes to 1½ hours, and preferably at 65° C. for approximately 1 hour. After the composition has cured, it can be removed from the mold to provide the conductive silicone contact 12 which typically has a resistivity of 10–15 ohm-cm. The silicone composition or mass 41 which is formed with the silver-coated glass rods 42 within has a resistivity ranging typically from 10–15 ohm-cm. The pad has a consistency somewhat like Jello and has a slightly tacky or sticky surface when felt by the human hand. It typically is harder with the silver particles therein than the gel by itself. It still has a relatively low durometer value ranging from 20 to 50 on the scale of 0 to 100 of a PTC Model 302 SL Hardness Tester made by Pacific Transducer Corporation of 2301 Federal Avenue, Los Angeles, Calif. 90064. The PTC scale making these durometer measurements used a spring-loaded cylindrical probe having a circular contact surface of one square centimeter and using 100 to 120 grams of force. The scale of 20 to 50 translates into a penetration of the contact element by the probe of 4 to 2½ millimeters respectively. By utilizing a slightly higher proportion of catalyst it is possible to obtain a slightly stiffer contact pad having a higher durometer value.

As shown in FIG. 7, the conductive rods 42 extend through all of the outer surfaces of the silicone contact including 31, 32 and 33 to make good electrical contact with the skin of the patient and the coating 18 of the button 17. Because of the thousands of conductive rods 42 extending through the surfaces of the contact element 12, excellent electrical contacts are made between the contact element 12 and any surface it engages.

In certain applications for electrodes where additional tackiness or stickiness is desired, a putty-like mass can be formed by adding less catalyst and curing at a higher temperature, as for example about 300° F. for a period of about an hour.

The desired resistivity can be relatively carefully controlled by measuring the resistivity of the mixture during the time that the silver-coated glass rods or fibers are being introduced into the mixture. As soon as the desired conductivity is reached, no further silver-coated fibers are added. It has been found that the mass which is produced for forming the contact 12, after curing, is very stable over a long period of time, as for example years. It also has a very sticky or tacky surface which is a very important attribute for use in making an electrode to contact the skin, as for example the skin of a human. The low durometer of the contact is also desirable because it permits the electrode to conform to the shape of the skin contours.

It has been found that the mixture can be kept indefinitely before curing by refrigerating the same at a suitable temperature, as for example at −25° to −45° C.

When it is desired to utilize the same it can be brought out of the refrigerator and mixed again immediately prior to pouring into a mold to be sure that the silver-coated fibers have not settled out. As soon as the mold is subjected to a curing temperature, the mixture begins to cure. The mass is also particularly desirable for use as a contact because in addition to being very stable it does not dry out or become brittle with time. Thus it has a non-drying characteristic.

Although silver-coated rods or flakes have been disclosed as being the most preferable material known at the present time, it is possible to use other materials which are good conductors, as for example pure silver, gold and the like. However, using the pure materials without there being a carrier is unduly expensive. Therefore, it is desirable to provide rods or fibers or flakes of the type hereinbefore described which are coated to provide the desired conductivity. In addition to silver and gold, other conductive metals, as for example nickel or copper, can be used. In addition, conductive materials such as graphite rods also can be utilized, even though there will be some sacrifice in conductivity. Conductivity as low as 100–200 ohm-cm can be achieved, which is within an acceptable range. Graphite, however, has a disadvantage in that graphite at the surface will have a tendency to rub off and leave a mark on the skin of the patient which may be undesirable to the patient. However graphite itself is inert and will not react to body fluids.

Although the electrode 11 has been discussed primarily for making ECG measurements, other skin type measurements such as EMG (electromyogram for muscle potential measurement), EEG (electroencephalogram for making brain wave measurements), and EOG (for measuring eye motion over the eyebrows). The electrodes can also be used for electrical stimulation as in TENS.

Figure 4:
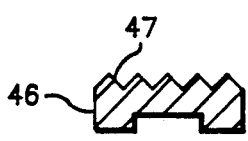
FIGS. 4, 5 and 6 are cross-sectional views of alternative embodiments of contact elements incorporating the present invention.
Figure 5:
Figure 6:
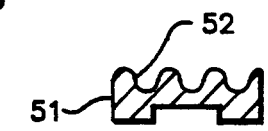

In order to permit the skin to breathe beneath a silicone contact the surface 33 can be roughened. Thus, as shown in FIG. 4, a contact element 46 is provided which has sawtooth ridges 44 extending transversely thereof. In FIG. 5, a contact element 48 is provided which has U-shaped parallel recesses 49 extending transversely thereof. In FIG. 6, a contact element 51 is provided which has arcuate recesses 52 extending transversely thereof. These ridges and grooves permit air to circulate over the skin, permitting the skin to breathe.

The silicone contact or contact element 12 has the following specifications when tested against American National Standard pre-gelled disposable ECG electrodes having an electrolyte.

| Parameter | AAMI Requirement | Applicant's Silicone Contact |
| --- | --- | --- |
| 1. Shelf Life | Use Before Date must be specified (typically 3 mos.) | >>one year |
| 2. AC Impedance | <2K Ω, for fresh electrodes | <5 Ω |
| 3. DC Offset Voltage | <100 mV after 1 minute | 0.00 V |
| 4. Offset Instability Internal Noise | <150 μV P-P in the Pass Band 0.15 Hz to 100 Hz | 0.00 V |
| 5. Defib. | <100 mV, 5 Sec. | 0.00 V |

| Parameter | AAMI Requirement | Applicant's Silicone Contact |
| --- | --- | --- |
| 6. Recovery Bias Current Tolerance | after Pulse <100 mV after 8 hours at 200 nA constant current | <1.0 μV |

The zero volts for DC offset, internal noise and defibrillation recovery arise because no electrolyte is present in the silicone contact of the present invention. The low impedance and the lack of an electrolyte reduces to a negligible value the voltage across the electrodes when subjected to a bias current.

Figure 8:
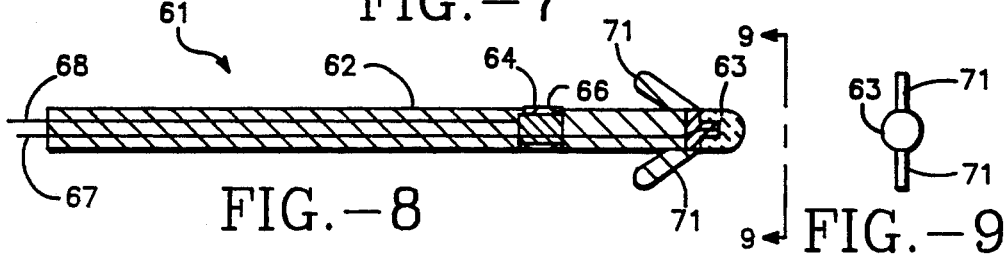
FIG. 8 is a partial side elevational view in cross section of a pacemaker lead incorporating contact elements of the present invention.
Figure 9:
FIG. 9 is an end elevational view looking along the line 9—9 of FIG. 8.

It should be appreciated that the conductive silicone contact 12 described in the present invention can be utilized in other applications. One other medical application would be for a pacemaker lead 61 as shown in FIG. 8. Such a lead 61 is comprised of a flexible elongate element 62 formed of a plastic. A conductive tip 63 formed of the conductive silicone material shown in FIG. 8 is bonded to a conductor 67 carried by the element 62. A conductive band 64 also formed of the conductive silicone material of the present invention is seated within an annular recess 66 in the elongate element 62 and is bonded to a lead 68. Because of the characteristics of the silicone material, as for example the tackiness and the low durometer, the conductive tip 63 and the conductive band 64 make an excellent contact with the heart muscle to have it fibrose onto the lead 61. In order to facilitate anchoring of the conductive tip 63, the pacemaker lead 61 can be provided with fishhook-like elements 71 made of the same material as the flexible element 62.

It is apparent from the foregoing that there has been provided a low impedance, low durometer, dry conforming contact element and a method for making the same as well as devices for utilizing the same. The contact element is formed of a material which is dry and remains tacky over a long period of time which makes it an excellent material to contact the skin for making various types of skin measurements. It also conforms to the contours of the skin. The contact element also can be formed with a serrated surface permitting the skin to breathe. The contact element can be worn for long periods of time as for example weeks without irritation to the skin. The wearer can bathe and take showers without removing the electrode or electrodes.

What is claimed is:

1. A contact comprised of a non-drying mass of non-conductive material having a low durometer and conductive elements dispersed in the mass of material in sufficient quantity to establish contact between the elements to provide a resistivity which is less than 100 ohm-cm, said conductive elements having an L over D ratio of 20 or less and greater than 2 and comprising more than 30% by weight of the contact.

2. A contact as in claim 1 wherein said conductive elements are formed of a material which is nonreactive to body fluids.

3. A contact as in claim 2 wherein said conductive elements are formed of a noble metal.

4. A contact as in claim 1 wherein said conductive elements are in the form of members of an inert material having a conductive coating formed thereon.

5. A contact as in claim 4 wherein said conductive coating is comprised essentially of a metal.

6. A contact as in claim 5 wherein said metal is silver and wherein the conductive elements have a silver content of at least 2 percent by weight.

7. A contact as in claim 1 wherein the mass of nonconductive material is a chemically inert polymer.

8. A contact as in claim 7 wherein said contact has a tacky surface which remains tacky over substantial periods of time.

9. A contact as in claim 7 wherein said polymer is an insulating gel.

10. A contact as in claim 1 having a durometer ranging from 20 to 50 on a PTC Model 302 SL Tester.

11. A contact as is claim 1 wherein the contact has zero volts for DC offset, internal noise and defibrillation recovery.

12. A contact as in claim 1 which has an AC impedance of less than five ohms.

13. A contact as in claim 1 having a putty-like consistency.

14. A contact comprised of a non-drying mass of nonconductive material having a low durometer and conductive elements dispersed in the mass of material in sufficient quantity to establish contact between the elements to provide a resistivity which is less than 100 ohm-cm, said conductive elements having an L over D ratio of 20 or less and greater than 2, said conductive elements having a size ranging from 15 to 100 microns in any dimension.

15. A contact comprised of a mass of nonconductive material having a low durometer and conductive elements dispersed in the mass of material in sufficient quantity to establish contact between the elements to provide a resistivity which is less than 100 ohm-cm, said contact having a surface with ridges extending transversely thereon to permit the skin of a patient to breathe.

16. In a low impedance electrode for engaging the skin of a patient, a pad having a surface, said pad being formed with a recess therein, a metallic button disposed within the recess and means securing the metallic button on the pad so that it remains with the pad, a conductive polymer contact disposed within said recess and engaging said button, said polymer contact having conductive elements therein and being characterized in that it has a resistivity of less than 100 ohm-cm, said conductive elements having an L over D ratio of 20 or less and greater than 2 and comprising more than 30% by weight of the polymer contact.

17. An electrode as in claim 16 together with a protective element enclosing said contact and an adhesive disposed between said protective element and said pad for retaining said protective element on said pad.

18. An electrode as in claim 16 together with lead means connected to said button for making electrical contact to the button.

19. In a low impedance electrode for engaging the skin of a patient, a pad having a surface, said pad being formed with a recess therein, a metallic button disposed within the recess and means securing the metallic button on the pad so that it remains with the pad, a conductive polymer contact disposed within said recess and engaging said button, said polymer contact having conductive elements therein and being characterized in that it has a resistivity of less than 100 ohm-cm, said conductive elements having an L over D ratio of 20 or less and greater than 2 and comprising more than 30% by weight of the polymer contact, said polymer contact having a low durometer in the range of 20 to 50 on PTC Model SL Tester, said polymer contact having a tacky surface.

20. In a pacemaker lead, a flexible elongate element having a distal extremity, a conductive tip formed on the distal extremity, said conductive tip being formed of a non-drying mass of conductive material having a low durometer and conductive elements disposed in the mass of material in sufficient quantity to establish contact between the elements to provide resistivity which is less than 100 ohm-cm, said conductive elements having an L over D ratio of 20 or less and greater than 2.

* * * * *